United States Patent [19]

Heinsohn et al.

[11] Patent Number: 5,209,858

[45] Date of Patent: May 11, 1993

[54] STABILIZATION OF CHOLINE AND ITS DERIVATIVES AGAINST DISCOLORATION

[75] Inventors: George E. Heinsohn, Elkton, Md.; Rudolf E. Svadlenak, Sunriver, Oreg.

[73] Assignee: E. I. Du Pont de Nemours and Company, Wilmington, Del.

[21] Appl. No.: 652,035

[22] Filed: Feb. 6, 1991

[51] Int. Cl.$^5$ .................. C07C 213/00; C09K 3/00; C09K 15/20
[52] U.S. Cl. .................. 252/1; 156/659.1; 252/189; 252/403; 252/545; 252/548; 514/642; 514/893; 564/293
[58] Field of Search ................ 252/1, 403, 189; 564/293

[56] References Cited

U.S. PATENT DOCUMENTS

| | | | |
|---|---|---|---|
| 2,217,711 | 10/1940 | Shappirio | 252/403 |
| 2,430,031 | 11/1947 | Shappirio | 252/403 X |
| 2,774,759 | 12/1956 | Blackett et al. | 564/293 X |
| 3,445,498 | 5/1969 | Cyba | 252/403 X |
| 4,575,455 | 3/1986 | Miller | 252/189 X |
| 4,629,613 | 12/1986 | Grosskinsky et al. | 252/403 X |
| 4,931,195 | 6/1990 | Cao et al. | 252/8.8 |

FOREIGN PATENT DOCUMENTS 59-134752 8/1984 Japan.

Primary Examiner—Richard D. Lovering
Attorney, Agent, or Firm—Robert B. Stevenson

[57] ABSTRACT

The stabilization of aqueous or alkanolic solutions of choline and derivative of choline against discoloration on aging by the addition of an unsubstituted hydroxylamine salt to the choline solutions at levels of less than 1 percent.

11 Claims, No Drawings

STABILIZATION OF CHOLINE AND ITS DERIVATIVES AGAINST DISCOLORATION

FIELD OF THE INVENTION

This invention relates to a method of stabilizing choline and choline derivatives against discoloration on aging. More particularly, the invention relates to aqueous or alkanolic choline solutions having improved coloring resistance. Still more particularly, the invention relates to the stabilization of aqueous or alkanolic choline and choline derivatives against discoloration on aging by the addition of an unsubstituted hydroxylamine salt to a choline solution at levels of less than 1 wt. percent.

BACKGROUND OF THE INVENTION

Choline, also known as choline base, is a colorless liquid and a strong organic base. Chemically, it is trimethyl(2-hydroxyethyl)ammonium hydroxide and can be represented by the formula $[(CH_3)_3NCH_2CH_2OH]^+OH^-$. It is not usually encountered as the free base but as a salt; the one most commonly used is chloride.

Choline chloride is an important nutritional substance, is used clinically in liver disorders and as a constituent in animal feeds. Choline base is especially suitable for use as a photoresist stripper. Aqueous and $C_1$-$C_8$ alcoholic solutions of choline are useful in electronic applications such as photoresist developing and stripping, anisotropic etching and cleaning silicon wafers, furnace tubes and the like.

Among the choline derivatives which have been or are being produced on a commercial scale, there may be mentioned choline hydroxide, choline chloride, choline bitartrate, choline dihydrogen citrate, choline bicarbonate, choline bisulfate, tricholine phosphate and tricholine borate. These derivatives and other unnamed derivatives as well as choline-like compounds in basic solutions can be stabilized in accordance with the present invention.

Choline base itself is ordinarily sold as an aqueous or methanolic solution which is nearly colorless when received from the manufacturer. There is a tendency to yellow, i.e., to decompose, particularly during shipment and storage. This tendency has the unwanted consequence of darkening and forming precipitates which impair the efficacy of the base as a developing or stripping agent. The color can be removed by treatment with activated carbon but this causes added expense and inconvenience to the user. Furthermore, choline treated in such fashion soon begins to form color again. To prevent or retard such decomposition and resulting discoloration with its consequences, it would be desirable to provide an inexpensive stabilizer for choline base that would not interfere with the intended use in any way and retain its water-white color over long periods of time.

SUMMARY OF THE INVENTION

We have now found that choline and its derivatives can be stabilized against discoloration on aging by the addition of an unsubstituted hydroxylamine salt to aqueous or alkanolic solutions of choline and choline derivatives at levels of less than 1 wt. percent.

Specifically, we have found that the adverse coloring effect resulting from the decomposition of choline and its derivatives in solutions containing them can be prevented, or at least substantially reduced, by incorporating in the solution a stabilizing concentration of a hydroxylamine salt. Thus, solutions containing choline or a derivative thereof and a stabilizing concentration of hydroxylamine salt have shelf life characteristics substantially better than unstabilized solutions. These stabilized solutions may be used for purposes already known in the art for unstabilized solutions and are particularly useful as a key ingredient in photoresist strippers.

DETAILED DESCRIPTION OF THE INVENTION

This invention is directed to solutions comprising choline base or a choline derivative, a solvent selected from the group consisting of water, aliphatic alcohols having up to eight carbon atoms, and mixtures thereof, and a stabilizing concentration of an additive, i.e., a stabilizer, namely, an unsubstituted hydroxylamine salt. Preferred solvents are water, methanol and mixtures of the two. Among the higher alcohols which may be used is 2-ethyl hexanol. Any of the $C_2$ to $C_8$ alcohols are operable. The concentration of choline or a derivative thereof in the solution of our invention may vary from 0.1% upwards to 50% by weight or higher. While the preferred hydroxylamine salts are sulfate and hydrochloride, any inorganic or organic acid salt of the base hydroxylamine may be employed in the practice of our invention. Illustrative of the salts there may be named nitrate, phosphate, acetate, lactate, glycolate and the like.

Choline stabilized in accordance with this invention is normally stored and shipped in a concentrated form, typically at 22 wt.% and up to a high of about 45 wt.%, to avoid the cost of shipping and storing excess water. The concentrate is diluted for use, as desired, to a sufficient concentration for accomplishing its particular intended purpose. When the choline concentration in water is less than 7%, the liquid is generally water-white and remains so for some months before the yellowing problem appears. When the choline concentration is raised to 45%, a methanolic solution of the stabilized choline solution is preferred over an aqueous solution. If the choline solution is made using methanol, the resulting product is found to have a longer stable shelf life than if otherwise prepared. A 45% aqueous solution of choline will begin to darken almost immediately after preparation.

EXAMPLE 1

A series of experiments are shown in Tables 1, 2, 3, 3a and 4 using 22% and 44% aqueous solutions of choline base which had been previously decolorized using Darco G-60 decolorizing carbon. The spent carbon was filtered off, leaving a water-white filtrate of choline. To portions of this filtrate were added the color stabilizer component, e.g., a salt of hydroxylamine in the indicated amounts. Sample vials containing the indicated percentages of stabilizer were stored at room temperature as well as in block heaters held at 50° and 70° C. for indefinite periods of time ranging from less than 1 day to 51 days. The color of each sample was first determined visually as a function of time. The results indicate that as little as 0.2% HAS is effective in reducing color formation. Concentrations are expressed as wt. percent.

TABLE 1

Stabilization of 22% Choline Base Against Discoloration at Room Temperature

| Sample | Wt. % HAS[1] | Days Elapsed | Appearance |
|---|---|---|---|
| 1 | 0.0 | >12 | Amber |
| 2 | 0.2 | <89 | WW[2] |
| 3 | 0.4 | " | " |

[1] HAS = Hydroxylamine sulfate
[2] WW = Water-white

TABLE 2

Stabilization of 22% Choline Base Against Discoloration at 50° C.

| Sample | Wt. % HAS | Days Elapsed | Appearance |
|---|---|---|---|
| 4 | 0.0 | <1 | Amber + ppt. |
| 5 | 0.2 | >14 | WW[1] |
| 6 | 0.4 | >112 | " |
| 7 | 0.6 | >100 | " |

[1] WW = Water-white

TABLE 3

Stabilization of 22% Choline Base Against Discoloration at 70° C.

| Sample | Wt. % HAS | Days Elapsed | Appearance |
|---|---|---|---|
| 8 | 0.0 | 1 | Amber + ppt. |
| 9 | 0.2 | 43 | Light Yellow |
| 10 | 0.4 | 43 | Light Yellow |

TABLE 3a

Stabilization of 44% Choline Base Against Discoloration at 70° C.

| Sample | Wt. % HAS | Days Elapsed | Appearance |
|---|---|---|---|
| 11 | 0.0 | 1 | Dark |
| 12 | 0.2 | 1 | Yellow |
| 13 | 0.4 | 4 | Light Yellow |
| 14 | 0.6 | 7 | Very Light Yellow |
| 15 | 0.8 | >92 | WW[1] |

[1] WW = Water-white

TABLE 4

Demonstration of the Near Equivalency of HAS* and HAC**

| Sample | Additive | Days Elapsed | Appearance |
|---|---|---|---|
| 16 | None | 2 | Amber + ppt. |
| 17 | 0.2% HAC | 41 | WW*** |
| 18 | 0.2% HAS | 30 | Slight Yellow |

*HAS = hydroxylamine sulfate, $(H_2NOH)_2 \cdot H_2SO_4$
**HAC = hydroxylamine hydrochloride, $H_2NOH \cdot HCl$
***WW = Water-white

EXAMPLE 2

T a sample of 44% methanolic choline base was added 0.2% hydroxylamine sulfate. To a second sample nothing was added. The samples were refulxed side by side at 65° C. The sample containing no additive became discolored in less than 6 hours while the stabilized sample showed no color change after 24 hours.

EXAMPLE 3

To a sample of 44% methanolic base was added 1% hydroxylamine acetate. To a second sample nothing was added. The samples were refluxed side by side at 65° C. The sample containing no additive became discolored in less than 6 hours while the stabilized sample showed no color change after 24 hours.

EXAMPLE 4

This example illustrates the use of stabilized choline and a derivative thereof in typical stripper formulations at the point of use and not as shipped to the formulators.

| A | |
|---|---|
| Choline hydroxide | 3.5% |
| Methanol | 13.3 |
| Ethylene diamine | 1.3 |
| Monoethanol amine | 77.5 |
| Tetramethyl ammonium hydroxide | 4.4 |
| B | |
| Choline hydroxide | 3.2% |
| Water | 12.9 |
| Ethylene diamine | 1.3 |
| Monoethanol amine | 78.2 |
| Tetramethyl ammonium hydroxide | 4.4 |
| C | |
| Tricholine phosphate | 3.4% |
| Water | 7.9 |
| Ethylene diamine | 1.4 |
| Monoethanol amine | 82.6 |
| Tetramethyl ammonium hydroxide | 4.7 |

The Example 4(C) illustrates that a stabilized choline derivative can be used in an admixture with a composition having hydroxyl ions at a high pH.

EXAMPLE 5

This example illustrates the stabilization of 22% aqueous choline base against discoloration at 50° C. using 1% hydroxylamine acetate. To a sample of 22% aqueous base was added 1% hydroxylamine. To a second sample nothing was added. The samples were refluxed side by side. The sample containing no additive became amber in 2 days and a precipitate formed. The stabilized sample showed no color after 30 days.

We claim:

1. A stabilized choline solution comprising choline or a salt thereof; a solvent selected from the group consisting of water, alkanols of 1 to 8 carbon atoms and mixtures thereof; and a stabilizing concentration of an unsubstituted hydroxylamine salt to prevent decomposition of said choline or salt thereof.

2. The solution of claim 1 wherein the concentration of choline or a choline salt is between 0.1% and 50% by weight of the solution.

3. The solution of claim 1 wherein the concentration of the hydroxylamine salt is less than 1%.

4. The solution of claim 1 wherein the solvent is water and the concentration of the hydroxylamine salt is between about 0.1% and 1.0% by weight of the solution.

5. The solution of claim 1 wherein the solvent is methanol and the concentration of the hydroxylamine salt between about 0.1% and 1%.

6. The solution of claim 1 wherein the hydroxylamine salt is hydroxylamine sulfate.

7. The solution of claim 1 wherein the hydroxylamine salt is hydroxylamine hydrochloride.

8. The solution of claim 1 wherein said choline salt is selected from the group consisting of choline chloride, choline bitartrate, choline dihydrogen citrate, choline bicarbonate, choline bisulfate, tricholine phosphate and tricholine borate.

9. The solution of claim 1 wherein said unsubstituted hydroxylamine salt is selected from the group consisting of hydroxylamine sulfate, hydroxylamine hydrochloride, hydroxylamine nitrate, hydroxylamine phosphate, hydroxylamine acetate and hydroxylamine glycolate.

10. The process of stabilizing a choline salt when stored in an admixture with a hydroxyl containing compound which comprises adding to the solution of said choline salt stored, an unsubstituted hydroxylamine salt at levels of less than 1% and a solvent selected from the group consisting of water, alkanols of $C_1$ to $C_8$ and mixtures thereof.

11. The process of claim 10 wherein the choline salt is tricholine phosphate and the hydroxyl containing compound is tetramethyl ammonium hydroxide.

* * * * *